US010980580B2

(12) United States Patent
Roberts

(10) Patent No.: US 10,980,580 B2
(45) Date of Patent: Apr. 20, 2021

(54) ARTHRODESIS/INTERCALLARY/SHORT STEM LIMB SALVAGE IMPLANT

(71) Applicant: Biomet Manufacturing, LLC, Warsaw, IN (US)

(72) Inventor: Mark Roberts, Plymouth, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 51 days.

(21) Appl. No.: 15/977,316

(22) Filed: May 11, 2018

(65) Prior Publication Data

US 2018/0344365 A1 Dec. 6, 2018

Related U.S. Application Data

(60) Provisional application No. 62/515,269, filed on Jun. 5, 2017.

(51) Int. Cl.
| | | |
|---|---|---|
| *A61F 2/38* | (2006.01) | |
| *A61B 17/72* | (2006.01) | |
| *A61F 2/28* | (2006.01) | |
| *A61F 2/30* | (2006.01) | |
| *A61B 17/00* | (2006.01) | |
| *A61B 17/74* | (2006.01) | |

(52) U.S. Cl.
CPC ............... *A61B 17/72* (2013.01); *A61F 2/28* (2013.01); *A61F 2/38* (2013.01); *A61F 2/3836* (2013.01); *A61B 17/7233* (2013.01); *A61B 17/74* (2013.01); *A61B 2017/00477* (2013.01); *A61F 2002/2825* (2013.01); *A61F 2002/2853* (2013.01); *A61F 2002/2892* (2013.01); *A61F 2002/3054* (2013.01); *A61F 2002/3069* (2013.01); *A61F 2002/3092* (2013.01); *A61F 2002/30331* (2013.01); *A61F 2002/30332* (2013.01); *A61F 2002/30383* (2013.01); *A61F 2002/30398* (2013.01); *A61F 2002/30433* (2013.01); *A61F 2002/30507* (2013.01); *A61F 2002/30622* (2013.01); *A61F 2002/30738* (2013.01); *A61F 2002/30878* (2013.01)

(58) Field of Classification Search
CPC .............. A61F 2/38–389; A61F 2/4241; A61F 2002/30624; A61F 2002/30662; A61F 2002/4243; A61F 2002/4251
See application file for complete search history.

(56) References Cited

U.S. PATENT DOCUMENTS

| 2,696,817 | A | * | 12/1954 | Prevo | ..................... | A61F 2/3804 |
| | | | | | | 623/20.12 |
| 4,538,306 | A | * | 9/1985 | Dorre | ..................... | A61F 2/3804 |
| | | | | | | 623/20.13 |

(Continued)

*Primary Examiner* — Nicholas J Plionis
*Assistant Examiner* — Steven J Cotroneo
(74) *Attorney, Agent, or Firm* — Schwegman Lundberg & Woessner, P.A.

(57) ABSTRACT

An implant apparatus for use in uniting a pair of bone segments, the apparatus including a first stem configured to be implanted in an intramedullary cavity of a first bone segment; a second stem configured to be implanted in an intramedullary cavity of a second bone segment; and a connector for connecting the first stem to the second stem, the connector including a first connector segment and a second connector segment, wherein the first connector segment and the second connector segment are coupled together at a lap joint connection.

14 Claims, 4 Drawing Sheets

(56) References Cited

U.S. PATENT DOCUMENTS

| | | | |
|---|---|---|---|
| 8,529,611 B2* | 9/2013 | Champagne | A61F 2/4225 606/328 |
| 2006/0173546 A1* | 8/2006 | Berelsman | A61F 2/3804 623/20.11 |
| 2006/0247786 A1* | 11/2006 | Ball | A61F 2/3804 623/20.13 |
| 2009/0149964 A1* | 6/2009 | May | A61B 17/155 623/20.15 |
| 2010/0222887 A1* | 9/2010 | Katrana | A61F 2/3804 623/20.11 |
| 2012/0143189 A1* | 6/2012 | Wolfson | A61F 5/013 606/55 |
| 2013/0345818 A1* | 12/2013 | Wagner | A61F 2/3804 623/20.12 |
| 2014/0018930 A1* | 1/2014 | Oster | A61B 17/8061 623/21.12 |

* cited by examiner

ARTHRODESIS/INTERCALLARY/SHORT STEM LIMB SALVAGE IMPLANT

CLAIM OF PRIORITY

This application claims the benefit of U.S. Provisional Patent Application Ser. No. 62/515,269, filed on Jun. 5, 2017, the benefit of priority of which is claimed hereby, and which is incorporated by reference herein in its entirety.

FIELD

The present subject matter relates generally to orthopedic surgical implant devices, and more specifically to prosthetic systems for replacement of parts of bones.

BACKGROUND

Knee arthrodesis is a procedure where the knee joint is fused between the tibia and the femur. In some case, this operation is advised in the case of severe, in particular infectious, complications following the fitting of articulated prostheses or following major trauma or bone ablations for the treatment of malignant tumors preventing the fitting of prostheses. In performing knee arthrodesis, stems are inserted into the intramedullary canals of the tibia and femur and then connected together to immobilize the joint.

In an intercalary procedure, it is necessary to excise intercalary bone from a long bone, that is, part of the diaphysis or bone shaft between the ends of the long bone, but it is not necessary to excise the ends of the long bone. For example, a portion of the shaft of the humerus may need to be removed to remove a malignancy, while the ends of the humerus defining parts of the shoulder and elbow joint may be healthy. Similarly, it may be necessary to excise part of the shaft of the tibia or femur while the ends of these bones are healthy. In these circumstances, the empty span between the ends of the bone must be replaced with a mid-shaft prosthesis that spans the distance between the native bone ends. For example, the mid-shaft prosthesis can include stems that fit into the intramedullary canals of the native bone ends and a body that extends between these stems to connect the stems.

In both the procedures discussed above, it can be difficult to implant such prostheses.

OVERVIEW

In example 1, an apparatus includes a first stem configured to be implanted in an intramedullary cavity of a first bone segment; a second stem configured to be implanted in an intramedullary cavity of a second bone segment; and a connector for connecting the first stem to the second stem, the connector including a first connector segment and a second connector segment, wherein the first connector segment and the second connector segment are coupled together at a lap joint connection.

In example 2, the apparatus of example 1 can include the first connector segment and the second connector segment defining complementary curved profiles at the lap joint connection.

In example 3, the apparatus of any of examples 1-2 can first connector segment and the second connector segment defining complementary profiles at the lap joint connection such that each of the first and second connector segments includes a cut out region to receive a corresponding projection section of the other of the first and second connector segments.

In example 4, the apparatus of example 3, can include the cut-out regions and projection sections of each of the first and second connector segments being curved to allow the first and second connector segments to be at least partially rotated relative to each other.

In example 5, the apparatus of any of examples 1-4 can include the first and second connector segments being couplable by a bolt extending through a bolt hole located in at least one of the first and second connector segments.

In example 6, the apparatus of any of examples 1-5 can include each of the first and second connector segments including a main connection portion including the lap joint and a shaft extending from the main connection portion, the shaft being configured to receive a modular porous collar.

In example 7, the apparatus of example 6 can include each of the first and second connector segments including a female taper region in the shaft configured to receive a male taper of one of the first or second stems or a male taper of an extender member located between the first or second stem and the first or second connector.

In example 8, the apparatus of any of examples 1-7 can include the first stem including a short stem assembly configured to be located proximate a native bone joint.

In example 9, the apparatus of example 8 can include the short stem assembly including first and second taper regions, a first taper region to connect to the first connector segment or an extender member and a second taper region configured to couple to a modular porous collar.

In example 10, the apparatus of example 9 can include the short stem assembly being configured such that a side plate can be mounted to the short stem assembly.

In example 11, an apparatus includes a first stem configured to be implanted in an intramedullary cavity of a first bone segment; a second stem configured to be implanted in an intramedullary cavity of a second bone segment; and a connector for connecting the first stem to the second stem, the connector including a first connector segment and a second connector segment, wherein the first connector segment and the second connector segment define complementary profiles at a lap joint connection such that each of the first and second connector segments includes a cut out region to receive a corresponding projection section of the other of the first and second connector segments, wherein the first and second connector segments are couplable by a bolt extending through a bolt hole located in at least one of the first and second connector segments.

In example 12, the apparatus of claim 11 can include the cut-out regions and projection sections of each of the first and second connector segments being curved to allow the first and second connector segments to be at least partially rotated relative to each other.

In example 13, the apparatus of any of examples 11-12 can include each of the first and second connector segments including a main connection portion including the lap joint and a shaft extending from the main connection portion, the shaft being configured to receive a modular porous collar.

In example 14, the apparatus of example 13 can include each of the first and second connector segments including a female taper region in the shaft configured to receive a male taper of one of the first or second stems or a male taper of an extender member located between the first or second stem and the first or second connector.

In example 15, the apparatus of any of examples 11-14 can include the implant being configured to be usable for either an arthrodesis procedure or an intercalary procedure.

In example 16, a method includes implanting a first stem in an intramedullary cavity of a first bone segment; implanting a second stem in an intramedullary cavity of a second bone segment; and coupling the first stem to the second stem using a connector, the connector including a first connector segment and a second connector segment, wherein the first connector segment and the second connector segment are coupled together at a lap joint connection.

In example 17, the method of example 16 can include the first connector segment and the second connector second defining complementary profiles at the lap joint connection such that each of the first and second connector segments includes a cut out region to receive a corresponding projection section of the other of the first and second connector segments.

In example 18, the method of example 17 can include the cut-out regions and projection sections of each of the first and second connector segments being curved to allow the first and second connector segments to be at least partially rotated relative to each other.

In example 19, the method of any of examples 16-18 can include the first and second connector segments being couplable by a bolt extending through a bolt hole located in at least one of the first and second connector segments.

In example 20, the method of any of examples 16-19 can include each of the first and second connector segments including a main connection portion including the lap joint and a shaft extending from the main connection portion, the shaft being configured to receive a modular porous collar.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
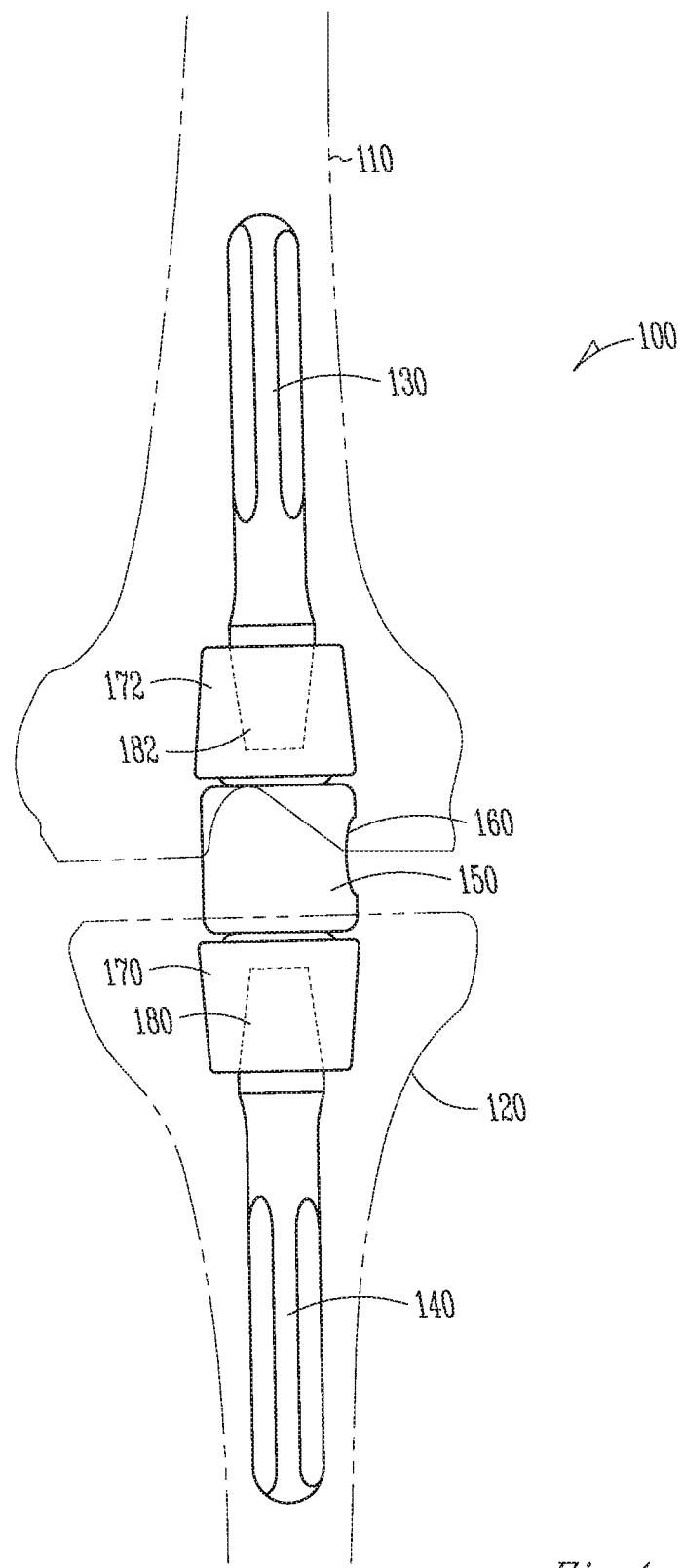
FIG. 1 shows an apparatus for performing an arthrodesis procedure in accordance with one embodiment.

FIG. 1 shows an apparatus 100 for performing an arthrodesis procedure in accordance with one embodiment. In an arthrodesis procedure a pair of bone segments, such as a femur 110 and a tibia 120, are united and the joint between the femur 110 and the tibia 120 is immobilized. This can be a temporary or permanent fusion.

Here the apparatus 100 generally includes a first stem 130 configured to be implanted in an intramedullary cavity of the femur 110, and a second stem 140 configured to be implanted in an intramedullary cavity of the tibia 120. The first stem 130 and the second stem are connected together with a connector 150 which is configured for connecting the first stem 130 to the second stem 140. As will be discussed in further detail below, the connector 150 includes a first connector segment and a second connector segment, wherein the first connector segment and the second connector segment are coupled together at a lap joint connection.

Figure 2:
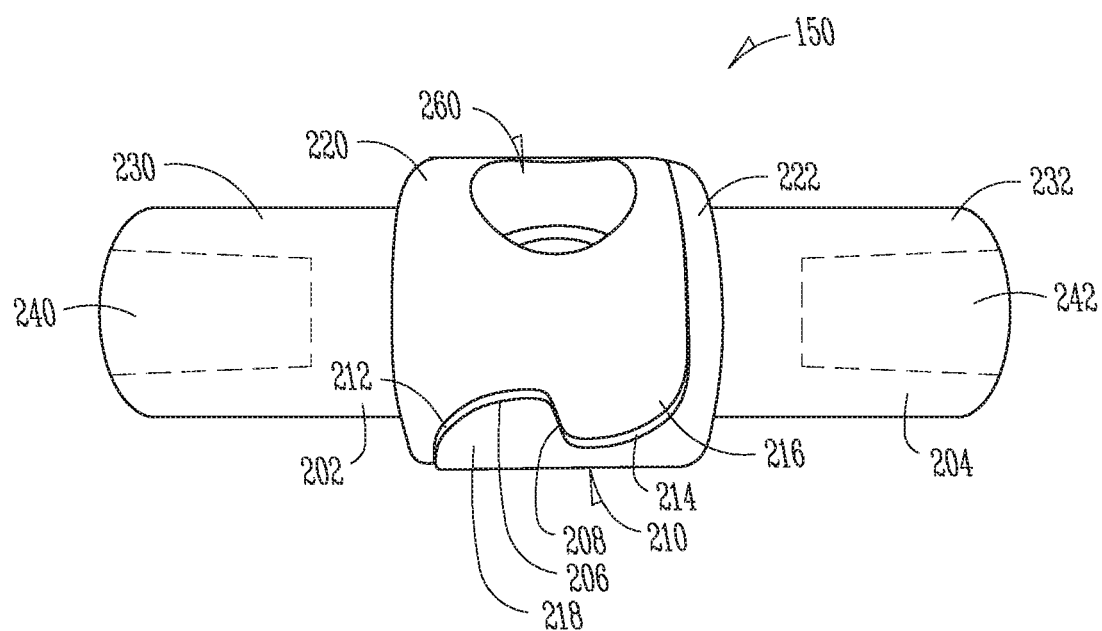
FIG. 2 shows side view of a connector usable in the apparatus of FIG. 1, in accordance with one embodiment.

Referring now also to FIG. 2, which shows side view of the connector 150 usable in the apparatus 100 in accordance with one embodiment, the connector 150 includes a first connector segment 202 and a second connector segment 204 which each define complementary curved profiles 206, 208 at a lap joint connection 210.

In one embodiment, the first connector segment 202 and the second connector segment 204 define complementary profiles at the lap joint connection 210 such that each of the first and second connector segments 202, 204 includes a respective cut-out region 212, 214 to receive a corresponding projection section 216, 218 of the other of the first and second connector segments 202, 204. Thus, the profiles of the first and second connector segments 202, 204 provide a wedge shaped lap joint connection that can then be fastened and locked together with a bolt 160 (FIG. 1) which can extend through a bolt hole 260 located in at least one of the first and second connector segments 202, 204.

Providing a lap joint connection as discussed herein allows for the connection to be made with minimal distraction of the bones, thus allowing for ease of assembly in the operating room. The two connector segments 202 and 204 can be connected to the stems 130, 140, for example, either before or after the stems 130 and 140 are implanted, and then laid one on top of the other without having to distract the bones and any corresponding soft tissue.

In one example, each of the first and second connector segments 202, 204 can include a main connection portion 220, 222 including the lap joint 210 and a shaft 230, 232 extending from the main connection portion 220, 222. The shaft 230, 232 can be configured to receive a modular porous collar 170, 172 (FIG. 1).

In one example, each of the first and second connector segments 202, 204 can include a female taper region 240, 242 in their shafts 230, 232 configured to receive a male taper 180, 182 of one of the first or second stems 130, 140 (FIG. 1) or a male taper of an extender member located between the first or second stem 130, 140 and the first or second connector segments 202, 204, as will be further noted below.

Figure 3:
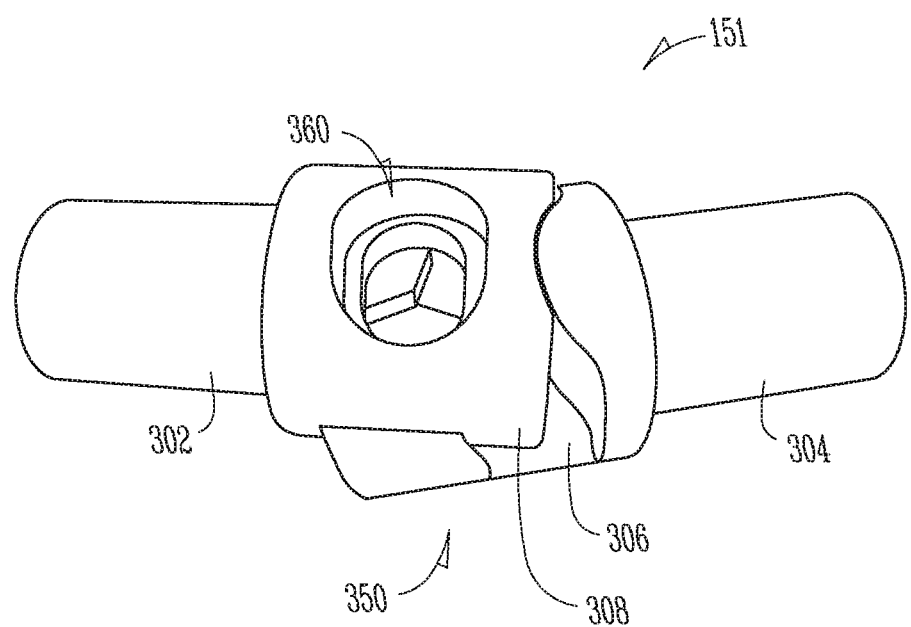
FIG. 3 shows a side view of a connector usable in the apparatus of FIG. 1, in accordance with one embodiment.

FIG. 3 shows a side view of a connector 151 usable in the apparatus 100, in accordance with one embodiment. The connector 151 is similar to connector 150 discussed above, and only major differences between the examples will be discussed.

Here, the connector 151 can include a first connector segment 302 and a second connector segment 304, where the first connector segment 302 and the second connector segment 304 can be coupled together at a lap joint connection 350.

In this example, the lap joint connection 350 is defined by the first connector segment 302 and the second connector segment 304 defining complementary profiles at the lap joint connection such that each of the first and second connector segments includes a cut out region 308 to receive a corresponding projection section 308 of the other of the first and second connector segments 302, 304. The cut-out regions 306 and projection sections 308 of each of the first and second connector segments 302, 304 are curved on their respective facing surfaces so as to allow the first and second connector segments 302, 304 to be at least partially rotated relative to each other. They can then be locked together with a bolt through a bolt hole 360. Such a rotatable design allows for a lap joint connection as discussed above and further allows for varus/valgus or flexion/extension correction by allowing the pieces to be rotated relative to each other and then locked into position.

Figure 4:
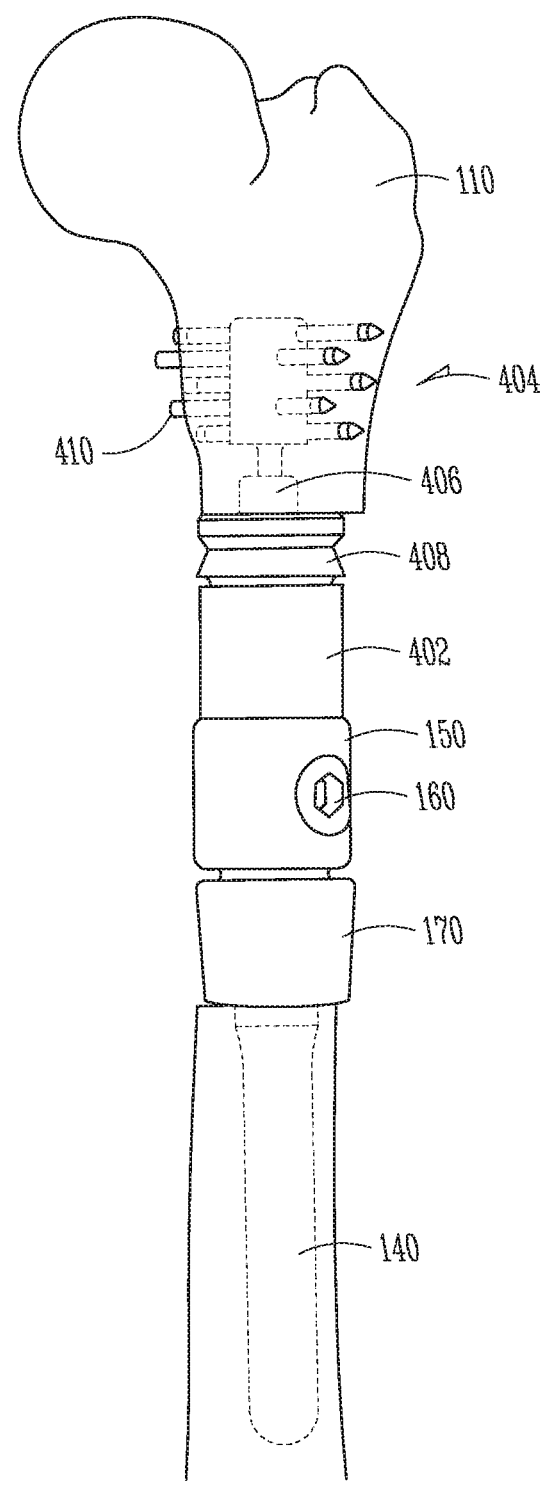
FIG. 4 shows an apparatus for performing an intercalary procedure, in accordance with one embodiment.

FIG. 4 shows an apparatus 400 for performing an intercalary procedure, in accordance with one embodiment. An intercalary procedure replaces a portion of a long bone. In this example, a femur 110 is shown, but the device can be used on other long bones.

In this example the intercalary apparatus can include the stem 140 configured to be implanted in an intramedullary canal of the femur 110. The connector 150, as described above, connects the stem 140 to a second stem. In this example, a short stem assembly 404 is used. Short stem assemblies can be used when the part of the bone removed is too close to the native joint. Thus, the stem 130 of FIG. 1 would not be applicable.

Here, the short stem assembly 404 can be coupled to the connector 150 with an extender member 402 between the two members. If only a small amount of bone is removed, an extender may not be needed. The short stem assembly 404 can include a main stem portion 406 and can include a porous bone collar 408 and fasters 410 such as nails or bone screws can extend through the short stem assembly 404.

Figure 5:
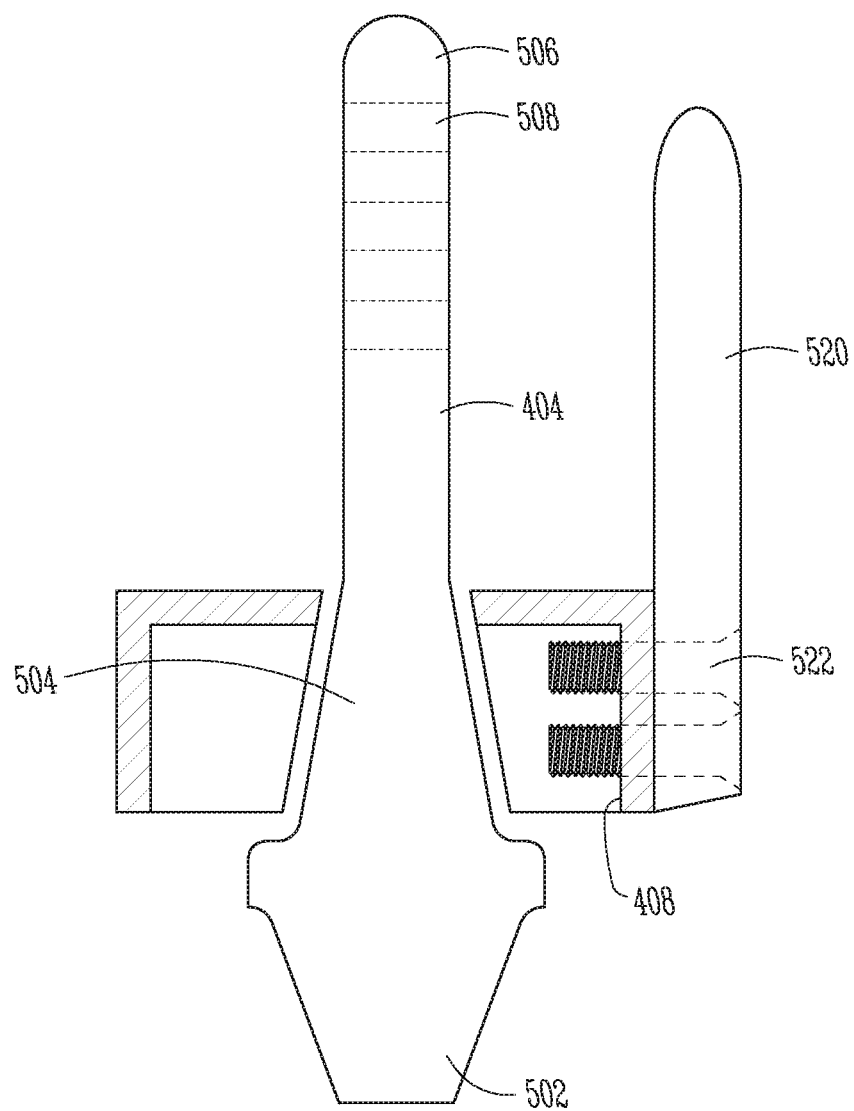
FIG. 5 shows a cross-section of a short stem usable with the apparatus of FIG. 4, in accordance with one embodiment.

FIG. 5 shows a cross-section of the short stem assembly 404 usable with the apparatus 400, in accordance with one embodiment. In this example, the short stem assembly 404 includes first and second taper regions 502, 504, where the first taper region 502 can be used to connect to the first connector segment of the connector 500 or to connect to the extender member 402, which can include a corresponding female taper. The short stem assembly 404 can include the second taper region 504 configured to couple to the modular porous collar 408. In an example, short stem assembly 404 is configured such that a side plate 530 can be mounted to the short stem assembly 404 for example, by using holes 502 extending through the side plate 530 and matching correspond holes in the porous collar 408 or the main stem body 406. One or more through-holes 508 can be provided in an upper shaft region 506 of the short stem assembly 404 to receive fasteners, as shown in FIG. 4.

In implanting the devices discussed herein, a surgeon can prepare the bone segments and the intramedullary cavities of the bone segments. Then the first stem can be implanted in in the intramedullary cavity of a first bone segment and the second stem can be implanted in the intramedullary cavity of a second bone segment. The two stems can be coupled together using a connector, where the connector can include a first connector segment and a second connector segment, wherein the first connector segment and the second connector segment are coupled together at a lap joint connection.

As explained above, many options are also possible. For instance the surgeon can add extenders, porous bone collars, or substitute a short stem assembly, if needed. Thus, the devices discussed about provide for a multi-faceted device that can be used in many indications including arthrodesis and intercalary.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An implant apparatus for use in uniting a pair of bone segments, the apparatus comprising:
   a first stem configured to be implanted in an intramedullary cavity of a first bone segment;
   a second stem configured to be implanted in an intramedullary cavity of a second bone segment; and
   a connector for connecting the first stem to the second stem, the connector including a first connector segment and a second connector segment, wherein the first connector segment and the second connector segment are coupled together at a lap joint connection, wherein the first connector segment and the second connector segment define complementary profiles at the lap joint connection such that each of the first and second connector segments includes a non-planar surface defining a proximal cut out region and a distal projection section which extends towards the other of the first and second connector segments, wherein the proximal cut-out region receives the corresponding distal projection section of the other of the first and second connector segments, and wherein the complementary profiles at the lap joint connection are defined such that when the first connector overlays the second connector, no surface of the second connector overlays any surface of the first connector.

2. The implant of claim 1, wherein the first connector segment and the second connector segment define complementary curved profiles at the lap joint connection.

3. The implant of claim 1, wherein the cut-out regions and projection sections of each of the first and second connector segments are curved to allow the first and second connector segments to be at least partially rotated relative to each other.

4. The implant of claim 1, wherein the first and second connector segments are couplable by a bolt extending through a bolt hole located in at least one of the first and second connector segments.

5. The implant of claim 1, wherein the each of the first and second connector segments includes a main connection portion including the lap joint and a shaft extending from the main connection portion, the shaft being configured to receive a modular porous collar.

6. The implant of claim 5, wherein each of the first and second connector segments includes a female taper region in the shaft configured to receive a male taper of one of the first or second stems or a male taper of an extender member located between the first or second stem and the first or second connector.

7. The implant of claim 1, wherein the first stem includes a short stem assembly configured to be located proximate a native bone joint.

8. The implant of claim 7, wherein the short stem assembly includes first and second taper regions, a first taper region to connect to the first connector segment or an extender member and a second taper region configured to couple to a modular porous collar.

9. The implant of claim 8, wherein the short stem assembly is configured such that a side plate can be mounted to the short stem assembly.

10. An implant apparatus for use in uniting a pair of bone segments, the apparatus comprising:
a first stem configured to be implanted in an intramedullary cavity of a first bone segment;
a second stem configured to be implanted in an intramedullary cavity of a second bone segment; and
a connector for connecting the first stem to the second stem, the connector including a first connector segment and a second connector segment, wherein the first connector segment and the second connector segment define complementary profiles at a lap joint connection such that each of the first and second connector segments includes a non-planar surface defining a proximal cut out region to receive a corresponding distal projection section of the other of the first and second connector segments, wherein the distal projection section extends towards the other of the first and second connector segments, wherein the first and second connector segments are couplable by a bolt extending through a bolt hole located in at least one of the first and second connector segments, and wherein the complementary profiles at the lap joint connection are defined such that when the first connector overlays the second connector, no surface of the second connector overlays any surface of the first connector.

11. The implant of claim 10, wherein the cut-out regions and projection sections of each of the first and second connector segments are curved to allow the first and second connector segments to be at least partially rotated relative to each other.

12. The implant of claim 10, wherein the each of the first and second connector segments includes a main connection portion including the lap joint and a shaft extending from the main connection portion, the shaft being configured to receive a modular porous collar.

13. The implant of claim 12, wherein each of the first and second connector segments includes a female taper region in the shaft configured to receive a male taper of one of the first or second stems or a male taper of an extender member located between the first or second stem and the first or second connector.

14. The implant of claim 10, wherein the implant is configured to be usable for either an arthrodesis procedure or an intercalary procedure.

* * * * *